(12) United States Patent
Eglseder, Jr.

(10) Patent No.: US 7,967,825 B2
(45) Date of Patent: Jun. 28, 2011

(54) CORONOID PROCESS FRACTURE FIXATOR

(75) Inventor: W. Andrew Eglseder, Jr., Owings Mills, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 851 days.

(21) Appl. No.: 11/912,138

(22) PCT Filed: Apr. 7, 2006

(86) PCT No.: PCT/US2006/012862
§ 371 (c)(1),
(2), (4) Date: Dec. 27, 2007

(87) PCT Pub. No.: WO2006/127146
PCT Pub. Date: Nov. 30, 2006

(65) Prior Publication Data
US 2008/0195097 A1    Aug. 14, 2008

Related U.S. Application Data

(60) Provisional application No. 60/674,508, filed on Apr. 25, 2005.

(51) Int. Cl.
*A61F 2/46* (2006.01)
(52) U.S. Cl. ............... 606/96; 606/86 R; 623/20.11

(58) Field of Classification Search ............... 606/53, 606/54, 57, 59, 86 R, 87, 88, 89, 96–98, 103–105; 623/20.11–20.13
See application file for complete search history.

(56) References Cited

U.S. PATENT DOCUMENTS

| | | | | |
|---|---|---|---|---|
| 3,949,428 A | * | 4/1976 | Cavendish et al. | 623/20.3 |
| 4,235,428 A | * | 11/1980 | Davis | 606/96 |
| 4,257,411 A | * | 3/1981 | Cho | 606/96 |
| 4,292,964 A | * | 10/1981 | Ulrich | 606/80 |
| 4,718,414 A | * | 1/1988 | Saunders et al. | 606/80 |
| 4,848,327 A | * | 7/1989 | Perdue | 606/54 |
| 4,901,711 A | * | 2/1990 | Goble et al. | 606/98 |
| 5,021,056 A | * | 6/1991 | Hofmann et al. | 606/86 R |
| 5,697,933 A | * | 12/1997 | Gundlapalli et al. | 606/96 |
| 6,179,800 B1 | | 1/2001 | Torrens | |
| 6,716,249 B2 | | 4/2004 | Hyde | |
| 6,719,793 B2 | | 4/2004 | McGee | |
| 7,153,309 B2 | * | 12/2006 | Huebner et al. | 606/96 |
| 2003/0009170 A1 | * | 1/2003 | Tornier | 606/87 |

* cited by examiner

*Primary Examiner* — Eduardo C Robert
*Assistant Examiner* — Lynnsy Schneider
(74) *Attorney, Agent, or Firm* — Evans & Molinelli PLLC

(57) ABSTRACT

A device, and method of using the device, for securing a coronoid process fragment to the remainder of a coronoid process of an ulna of a patient at a site of fracture, wherein the device comprises a frame component and at least two guiding components.

1 Claim, 2 Drawing Sheets

CORONOID PROCESS FRACTURE FIXATOR

CROSS REFERENCE TO RELATED APPLICATIONS

This application is a national phase application of international patent application no. PCT/US2006/012862, filed Apr. 7, 2006, which claims benefit of U.S. provisional patent application no. 60/674,508, filed Apr. 5, 2005, the contents of which are hereby incorporated by reference in their entireties.

TECHNICAL FIELD OF THE INVENTOR

The present invention relates to a method and device for securing a coronoid process fragment to the remainder of a coronoid process of an ulna bone at a site of fracture during surgical repair of a coronoid process fracture in the elbow joint of a patient. The present invention also relates to a method for repairing a coronoid process fracture of an ulna bone of a patient.

BACKGROUND OF THE INVENTION

The ulna is a long bone, prismatic in form, that is situated at the medial side of the forearm, parallel with the radius. The ulna is divisible into a body and two extremities. Its upper extremity, of great thickness and strength, forms a large part of the elbow-joint; the bone diminishes in size from above downward, its lower extremity being very small, and excluded from the wrist-joint by the interposition of an articular disk.

As illustrated in FIG. 1, the coronoid process 220 is a triangular eminence projecting forward from the upper and front part of the ulna 200, which forms a portion of the elbow joint. The base of the coronoid process is continuous with the body of the bone, and of considerable strength. Its apex is pointed, slightly curved upward, and, in flexion of the forearm, is received into the coronoid fossa of the humerus. Its upper surface is smooth and concave, and forms the lower part of the semilunar notch. Its antero-inferior surface is concave and marked by a rough impression for the insertion of the brachialis.

The coronoid process, among other functions, helps to resist posterior elbow subluxation. Fractures of the coronoid process of the ulna can occur in association with posterior dislocation of the elbow and valgus instability, since the medial collateral ligament (MCL) of the elbow inserts into the fracture fragment. Left untreated, the elbow joint of a patient can become unstable, stiff, and painful. In fact, stiffness is a common problem following this injury, as are post traumatic degenerative joint changes. In particular, patients with fracture of more than half of the coronoid process can lose over half of their range of elbow flexion-extension, and as few as one in five patients can expect to have a satisfactory recovery of function.

Accordingly, there remains a need for improved devices and methods for repairing coronoid process fractures in such a manner that the likelihood of recreating or reproducing a pain-free and fully functional elbow joint is maximized. It is an object of the present invention to provide such a device. This and other objects and advantages, as well as additional inventive features, will become apparent from the detailed description provided herein.

BRIEF SUMMARY OF THE INVENTION

The present invention provides a device for securing a coronoid process fragment to the remainder of a coronoid process of an ulna bone of a patient at a site of fracture during surgical repair of a coronoid process fracture. The device comprises a frame component and at least two guiding components. The frame component comprises at least one anterior traversing element that extends across the anterior side of the ulna of a patient, at least one posterior traversing element that extends across the posterior side of the ulna of the patient, and at least one connector element that operably connects the at least one anterior and the at least one posterior traversing elements in such a manner that the distance between the at least one anterior and the at least one posterior traversing elements is adjustable. The at least two guiding components each comprise (i) an anterior hollow guide element, which is situated on at least one anterior traversing element in proximity to the site of fracture and is positionable such that it contacts and secures the coronoid process fragment to the remainder of the coronoid process of the ulna, and through which a surgical device can be passed, and (ii) a posterior hollow guide element, which is situated on at least one posterior traversing element and is positionable such that it contacts a site on the posterior side of the ulna, and through which a surgical device can be passed. The anterior and posterior hollow guide elements of each guiding component collectively define formable surgical repair channels through the coronoid process fragment and the remainder of the ulna for use in repair of the coronoid process fracture.

The present invention also provides a method for securing a coronoid process fragment to the remainder of a coronoid process of an ulna of a patient at a site of fracture using the device described herein. The method comprises positioning the device such that the frame component extends across the ulna of the patient such that the anterior hollow guide elements of the at least two guiding components of the device are positioned in proximity to the site of fracture, and adjusting the distance between the at least one anterior traversing element and the at least one posterior traversing element of the frame component, such that the anterior hollow guide elements of the at least two guiding components contact and substantially secure the coronoid process fragment to the remainder of the coronoid process of the ulna, and the posterior hollow guide elements of the at least two guiding components contact the posterior side of the ulna. The method then comprises forming at least two surgical repair channels through the coronoid process fragment and at least a portion of the ulna by passing a surgical device through the anterior hollow guide elements or the posterior hollow guide elements of the at least two guiding components, and fixing the coronoid process fragment to the remainder of the coronoid process through use of a surgical binding device in the surgical repair channels.

DETAILED DESCRIPTION OF THE PRESENT INVENTION

The present invention provides a device for securing a coronoid process fragment to the remainder of a coronoid process of an ulna bone of a patient at a site of fracture during surgical repair of a coronoid process fracture. The device comprises a frame component and at least two guiding components. The frame component comprises at least one anterior traversing element that extends across the anterior side of the ulna of a patient, at least one posterior traversing element that extends across the posterior side of the ulna of the patient, and at least one connector element that operably connects the at least one anterior and the at least one posterior traversing elements in such a manner that the distance between the at least one anterior and the at least one posterior traversing elements is adjustable. The at least two guiding components each comprise (i) an anterior hollow guide element, which is situated on at least one anterior traversing element in proximity to the site of fracture and is positionable such that it contacts and secures the coronoid process fragment to the remainder of the coronoid process of the ulna, and through which a surgical device can be passed, and (ii) a posterior hollow guide element, which is situated on at least one posterior traversing element and is positionable such that it contacts a site on the posterior side of the ulna, and through which a surgical device can be passed. The anterior and posterior hollow guide elements of each guiding component collectively define formable surgical repair channels through the coronoid process fragment and the remainder of the ulna for use in repair of the coronoid process fracture.

Figure 1:
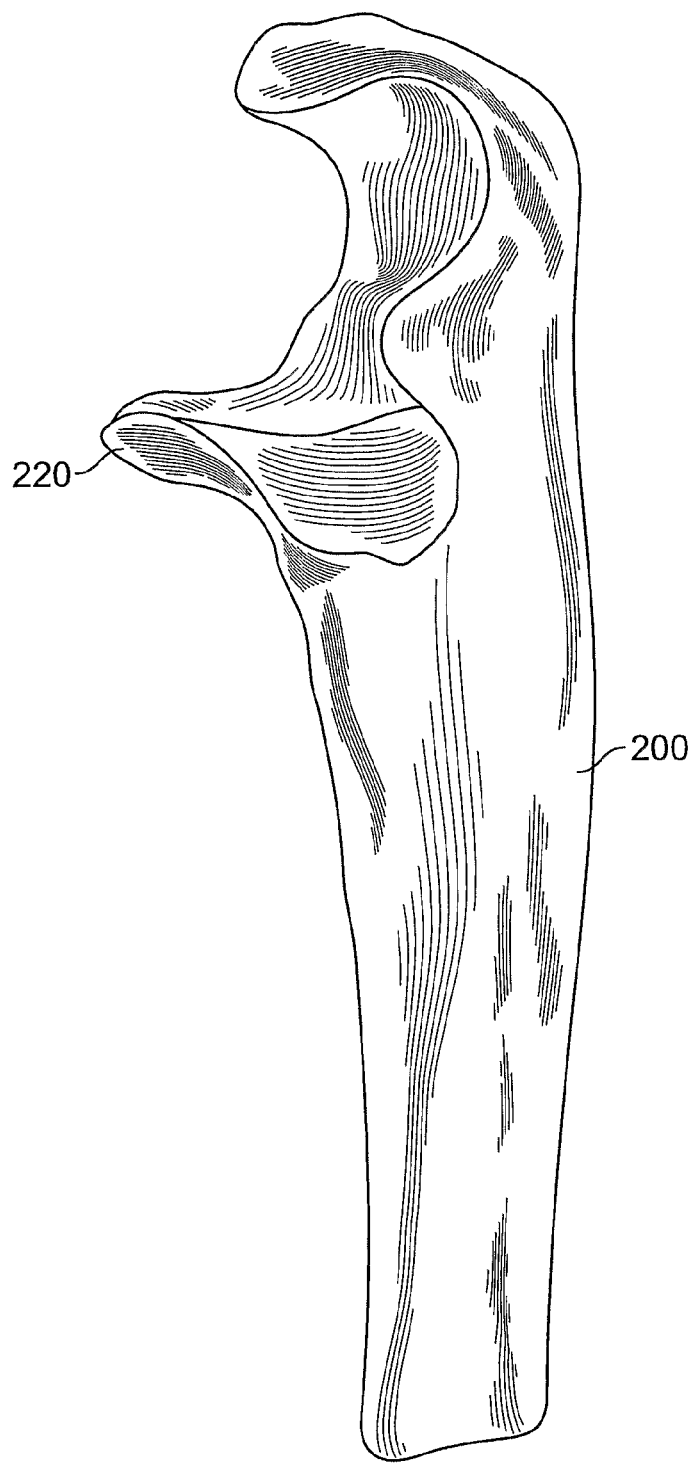
FIG. 1 is a schematic of the upper portion of a typical ulna bone with coronoid process.
Figure 2:
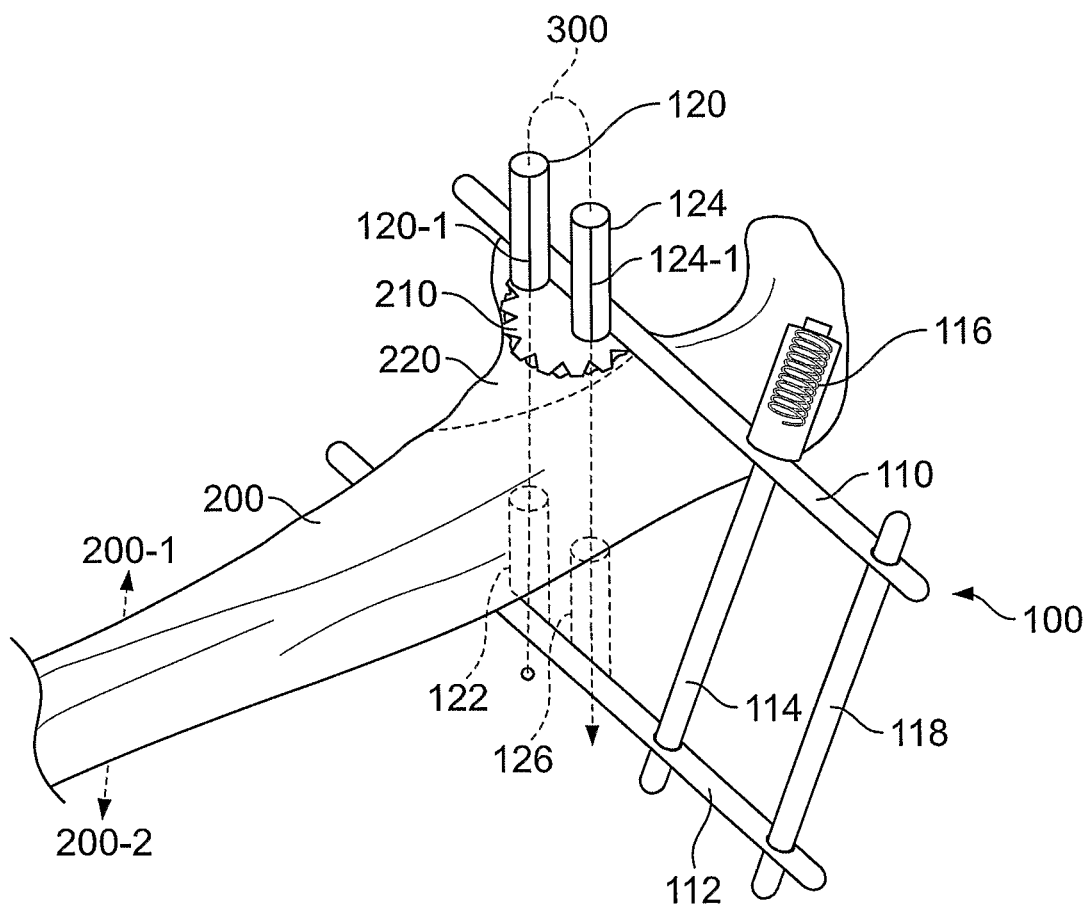
FIG. 2 is a diagram illustrating an exemplary device in accordance with the present invention positioned around an ulna bone having a coronoid process fracture.

FIG. 2 illustrates a device in accordance with the present invention. As illustrated, device 100 comprises a frame component that extends across the ulna 200 of a patient. In particular, device 100 comprises anterior traversing element 110, which extends across the anterior side of the ulna 200-1 of a patient, posterior traversing element 112, which extends across the posterior side of the ulna 200-2 of the patient, connector element 114, which operably connects anterior traversing element 110 and posterior traversing element 112 and which is usable by an operator for increasing or decreasing the distance between anterior and posterior traversing elements 110 and 112 through manipulation of adjustable knob 116. Device 100 also can comprise an additional stabilizing element 118. Moreover, device 100 comprises anterior hollow guide elements 120 and 124 having suture or wire removal guide slots 120-1 and 124-1, respectively, which extend from anterior traversing element 110 and which contact and secure coronoid process fragment 210 to the remainder of the coronoid process 220 of the ulna 200 of the patient during surgical repair of a coronoid process fracture; and posterior hollow guide elements 122 and 126, which extend from posterior traversing element 112 and which contact posterior sites of the ulna 200. FIG. 1 also illustrates an example path of a suture or wire 300 that is passable by an operator, for example, up through a formable (e.g., drillable) surgical repair channel defined by posterior hollow guide element 122 and anterior hollow guide element 120 and then down through a formable surgical repair channel defined by anterior hollow guide element 124 and posterior hollow guide element 126.

For purposes of discussion herein, anatomically directional terms are defined herein as follows. The human body is regarded as standing erect, eyes looking straight forward, arms by the sides, and the palms of the hands and toes directed forward. Three pairs of relative terms are used, herein, to express the orientation of the device used in the context of the pending application, in relation to the arm of a patient: "anterior" is defined herein to mean 'front' with regards to the orientation of the body; "posterior" is defined herein to mean 'back'; "medial" is defined herein to mean 'nearer the median plane of the body'; "lateral" is defined herein to mean 'farther from the median plane of the body'; "proximal" is defined herein to mean 'nearer the trunk of the body'; and "distal" is defined herein to mean 'farther from the trunk of the body'.

For example, in the above-described anatomical position, the palm of the hand is the anterior surface of the hand. In other words, no matter what position the hand may assume, the palm is still spoken of herein as the anterior surface because that is the surface, which faces anteriorly in the anatomical position. Moreover, while the hand is at the distal end of the arm, the shoulder is at the proximal end of the arm.

The frame component of the device described herein can be configured in any suitable manner. In one embodiment, for example, the frame component comprises at least two traversing elements that extend across substantially opposing or opposing portions or sides of the ulna of a patient with respect to each other. In another embodiment, the frame component comprises at least one anterior traversing element that extends across a substantially anterior or anterior side of the ulna of a patient and at least one posterior traversing element that extends across a substantially posterior or posterior side of the ulna of a patient. In this regard, it is preferable that at least one anterior and at least one posterior traversing element extend across substantially opposing or opposing portions or sides of the ulna of a patient with respect to each other, wherein the substantially opposing or opposing sides of the ulna are substantially anterior or anterior and substantially posterior or posterior to the ulna, respectively, and in a suitable position for fracture repair. It is also preferable for the at least one anterior traversing element and for the at least one posterior traversing element to extend in a substantially medial-lateral or medial-lateral direction (i.e., in a direction that is substantially perpendicular or perpendicular to the ulna of the arm of a patient) across the anterior and posterior sides of the ulna of a patient, respectively. The frame component can comprise any suitable number of traversing elements needed for a particular surgical process. In particular, for example, the frame component can comprise at least three, at least four, or even at least six traversing elements.

The at least one anterior and at least one posterior traversing elements of the device described herein can be linear or curvilinear in shape, and can be substantially parallel, parallel, or non-parallel in orientation with respect to each other. The frame component also can be constructed of any suitable material that provides a lightweight, rigid, and supportive structure for use by an operator during a surgical process, as is understood by those of ordinary skill in the art. It is suitable, in this regard, for example, for the frame component to be constructed of a metal (e.g., hollow metal).

The frame component of the device can also comprise at least one connector element that operably connects the at least one anterior and the at least one posterior traversing elements of the frame component (e.g., on the lateral side of the ulna of a patient). In the embodiment illustrated in FIG. 2, for example, the device 100 comprises connector element 114, which extends in a substantially perpendicular or perpendicular direction as compared to anterior traversing element 110 and posterior traversing element 112 and which is operably connected to anterior traversing element 110 and posterior traversing element 112. In particular, in this embodiment, connector element 114 is immovably affixed to posterior traversing element 112 and is slidably affixed to anterior traversing element 110 (e.g., by passing through an aperture in anterior traversing element 110), which accordingly can be made to slide down the length of connector element 114 in the direction of posterior traversing element 112, for example, through use of adjustable know 116 (e.g., that is spring-loaded and that engages a threaded portion of the substantially perpendicular or perpendicular element 114) that is situated on the anterior end of connector element 114 and which, in this manner, can be used by an operator to increase or decrease the distance between anterior and posterior traversing elements 110 and 112, such that, for example, the operator is able to "clamp down" on the ulna 200 of the patient with anterior and posterior traversing elements 110 and 112. Such a "clamping" can be accomplished, for example, by decreasing the space between anterior and posterior traversing elements 110 and 112 to such a degree that anterior hollow guide elements 120 and 124 and posterior hollow guide elements 122 and 126 make contact with coronoid process fragment 210 and ulna 200, respectively. The "distance between the at least one anterior and the at least one posterior traversing elements," in this regard, is defined herein to mean the average distance between points on at least one anterior traversing element and corresponding points on at least one posterior traversing element, e.g., as measured in an anterior to posterior direction. It is also suitable, in this regard, for the adjustable knob to control the distance (e.g., anterior-posterior distance) between at least two traversing elements on opposing sides of the arm of a patient, while at least one traversing element (e.g., on the anterior side of the arm) is unaffected in position by manipulation of the adjustable knob. For example, anterior and posterior traversing elements can be manipulated to "clamp down" on the ulna of a patient, while at least one anterior or at least one posterior traversing element (e.g., having a guide post for surgical device attached thereto) does not change in its position with respect to the ulna (e.g., but which can have a separate operably-attached element for controlling its position).

The device described herein can also comprise at least one stabilizing element for minimizing or preventing the movement of the at least one anterior and at least one posterior traversing elements and other components of the device in relation to one another during a surgical process. An example of such a stabilizing element is illustrated as element 118 in FIG. 2. Stabilizing element 118, in this regard, can be immovably affixed to posterior traversing element 112 and slidably affixed to anterior traversing element 110. Alternatively, stabilizing element 118 can be slidably affixed to posterior traversing element 112 and immovably affixed to anterior traversing element 110. It is also suitable for the relative placement of stabilizing element 118 and connector element 114 to be opposite of that illustrated in FIG. 2, such that, for example, connector element 114 is situated at the lateral ends of anterior traversing element 110 and posterior traversing element 112, and stabilizing element 118 is situated at a more medial location in relation to connector element 114.

The anterior hollow guide elements of the guiding components of the device described herein can function to contact, secure, and/or hold a coronoid process fragment to the remainder of the coronoid process of an ulna of a patient, as well as to secure the device described herein to the anterior side of the ulna and to provide guide posts for surgical devices (e.g., surgical binding devices) to be passed. The posterior hollow guide elements of the guiding components, on the other hand, can function to secure the device to the posterior side of the ulna, as well as to provide guide posts for surgical devices (e.g., surgical binding devices) to be passed. The anterior and posterior hollow guide elements are preferably cylindrical in shape and have a hollow interior channel through which one or more surgical devices can be passed by an operator (e.g., a surgeon or a computerized machine). "Surgical devices," in this regard, can be any surgical drill, surgical binding device (e.g., sutures, wires, suturing devices, suturing guides, wiring devices, wiring guides, screws, or any suitable device or compound for the internal fixation of two or more bone fragments together), or any other device that is known in the art to fixate, repair, and/or assist in repairing a site of bone fracture. In one embodiment, for example, two anterior hollow guide elements extending from an anterior traversing element are positioned such that they make contact with a coronoid process fragment and secure the coronoid process fragment atop the remainder of a coronoid process of an ulna of a patient (e.g., at a site where the coronoid process fragment had originally been situated prior to fracture and/or dislocation), while two posterior hollow guide elements make contact with sites on the posterior side of the ulna.

The anterior and posterior hollow guide elements can be positioned to make contact with the coronoid process fragment and the posterior side of the ulna, respectively, for example, by decreasing the distance between the anterior and posterior traversing elements on which the guide elements are situated. In this embodiment, an operator (e.g., a surgeon) can next pass a surgical device (e.g., a surgical drill) through the hollow interior channels of the anterior and/or the posterior hollow guide elements of both guiding components, such that two surgical repair channels (e.g., co-linear surgical repair channels) are created in the coronoid process fragment, the remainder of the coronoid process, and/or the ulna. The operator can then pass one or more surgical binding devices (e.g., sutures or wires), for example, as illustrated in FIG. 2, up through the surgical repair channel drilled in a prior step through anterior and posterior hollow guide elements 120 and 122, respectfully, and then down through the surgical repair channel drilled in a prior step through the anterior and posterior hollow guide elements 124 and 126, respectively, or vice versa. It is suitable, in this embodiment, for anterior hollow guide elements 120 and 124 to have suture or wire removal slots 120-1 and 124-1, respectively, so that the suture or wire that is threaded by an operator through the anterior hollow guide elements can be removed from the hollow interior channels of anterior hollow guide elements 120 and 124 via removal slots 120-1 and 124-1, respectively, in such a manner that the integrity of the suture or wire is not adversely affected. An operator can then tie, fasten, or secure the ends of the sutures or wires 300 together, thus securing or fixing the coronoid process fragment to the remainder of the coronoid process. In another embodiment, an operator can pass a surgical device (e.g., one or more screws) through anterior hollow guide element 120 and/or anterior hollow guide element 124, and into the coronoid process fragment and the remainder of the coronoid process, thus securing them together.

The anterior and posterior guide elements of each guiding component can secure the frame component of the device in a substantially fixed or fixed position relative to the ulna or arm of the patient, for example, by maintaining contact and/or exerting pressure on substantially opposing or opposing points of the arm of the patient, e.g., on the coronoid process fragment and the posterior side of the ulna. In this manner, movement of the frame component can be substantially prevented or prevented in relation to the arm of the patient, e.g., during a surgical procedure. It is also suitable, in this regard, for at least one hollow guide element, at least two hollow guide elements, at least four hollow guide elements, or at least six hollow guide elements to be situated on (or extend from) at least one anterior traversing element on the anterior side of the arm of a patient and for at least one hollow guide element, at least two hollow guide elements, at least four hollow guide elements or at least six hollow guide elements to be situated on (or extend from) at least one traversing element.

The anterior and posterior hollow guide elements of each guiding component of the device can be situated at any suitable locations on the anterior and posterior traversing elements, respectively. It is preferable, in this regard, for at least one anterior hollow guide element of each guiding component to be situated at a site on at least one anterior traversing element, which is in proximity to a site of coronoid process fracture, such that the anterior hollow guide elements can be positioned to contact and secure a coronoid process fragment to the remainder of the coronoid process of an ulna. The at least one posterior hollow guide elements of each guiding component are preferably situated at sites on at least one traversing element, which is in proximity to the posterior side of the ulna, such that the posterior hollow guide elements can be positioned to contact sites on the posterior side of the ulna. The anterior and posterior hollow guide elements of each guiding component can be "positionable" in any suitable manner. It is suitable, for example, for the hollow guide elements of each guiding component to be positionable via manipulation of adjustable knob 116 (see FIG. 2), which controls the distance between at least two traversing elements, such that, for example, the decreasing of the distance between at least one anterior and at least one posterior traversing elements causes the hollow guide elements situated on (or extending from) at least one traversing element in proximity to a surgical site to be positioned into the surgical site to an extent at which they make contact with the coronoid process or a coronoid process fragment. Moreover, it is suitable, for example, for at least one hollow guide element to be positionable via manipulation of an adjustable knob that is separate and distinct from adjustable knob 116. In a preferred embodiment, as illustrated in FIG. 2, anterior hollow guide elements 120 and 124 are situated at points on anterior traversing element 110 that are substantially opposite or opposite (e.g., coordinating or corresponding points) from the points on posterior traversing element 112, at which posterior hollow guide elements 122 and 126, are situated, respectively. In this regard, the hollow interior channels of the anterior and posterior hollow guide elements of each guiding component preferably define an imaginary line through the coronoid process fragment, the remainder of the coronoid process, and the ulna (referred to herein as a "formable surgical repair channel"), along which a surgical device can be passed to create surgical repair channels.

The anterior and posterior hollow guide elements of each guiding component can be constructed of any suitable durable material (such as hollow metal tubes), which stably functions in a surgical process, as is understood in the art. It is preferable, in this regard, for the anterior and posterior hollow guide elements to be constructed of a material that is appropriate for use in contacting and/or being partially inserted into bone material (e.g., a bone fragment, such as a coronoid process fragment) and to act as surgical device (e.g., surgical binding device) guides.

The device discussed herein can further comprise any additional attachment site and/or guide post. It is suitable, for example, for the device used in the context of the present invention to comprise an attachment point and/or guide post for suturing devices, arthroscopic devices, sources of light, and/or any other elements that are useful in a surgical procedure, as is understood in the art.

The present invention also provides a method for securing a coronoid process fragment to the remainder of a coronoid process of an ulna of a patient at a site of fracture using the device described herein. The method comprises positioning the device such that the frame component extends across the ulna of the patient such that the anterior hollow guide elements of the at least two guiding components of the device are positioned in proximity to the site of fracture, and adjusting the distance between the at least one anterior traversing element and the at least one posterior traversing element of the frame component, such that the anterior hollow guide elements of the at least two guiding components contact and substantially secure the coronoid process fragment to the remainder of the coronoid process of the ulna, and the posterior hollow guide elements of the at least two guiding components contact the posterior side of the ulna. The method then comprises forming at least two surgical repair channels through the coronoid process fragment and at least a portion of the ulna by passing a surgical device through the anterior hollow guide elements or the posterior hollow guide elements of the at least two guiding components, and fixing the coronoid process fragment to the remainder of the coronoid process through use of a surgical binding device in the surgical repair channels.

The method can be utilized in conjunction with any type of fracture of the coronoid process. In particular, for example, the method can be utilized in conjunction with a Type 1, Type 2, or Type 3 fracture of the coronoid process. Moreover, the method can be utilized in conjunction with any fracture of a coronoid process that is accompanied by a partial dislocation or complete dislocation of one or more fragments of the coronoid process. Moreover, in this regard, the method can be utilized during any portion of a surgical process, such as, for example, during drilling, suturing, screwing, threading of sutures and/or wires, and/or during preparation therefore, of a coronoid process fragment to a remaining portion of the coronoid process. The steps involved in creating a surgical repair channel in bone and bone fragments, as well as the steps involved in internally fixating bones, are well understood in the art.

While the device and method described herein are largely discussed herein in the context of repairing, fixating, or securing a coronoid process fragment to the remainder of a coronoid process of an ulna bone of a patient, one of ordinary skill in the art would understand that the method also can be utilized for fixating, securing, repairing, and/or replacing any fractured or dislocated bone fragment (e.g., any bone projection or process that is akin to the coronoid process of the ulna and elbow joint) to the corresponding region of a bone where the fracture and dislocation occurred. In particular, for example, the device and method described herein also can be employed to fixate, secure, repair, and/or replace a fractured or dislocated bone fragment from any long bone of the limbs, such as, for example, the humerus, ulna, radius, femur, tibia, or fibula. In this regard, for example, the device and method described herein can be employed to fixate, secure, repair, and/or replace a fractured or dislocated bone fragment to the proximal or distal end of the humerus bone of a patient, such as, for example, a capitellum bone fragment, a medial epicondyle bone fragment, a lateral epicondyle bone fragment, and/or a humeral head bone fragment. Moreover, the device and method can be used, for example, to fixate, secure, repair, and/or replace a fractured or islocated bone fragment to the proximal head of the radius. Moreover, the device and method can be used, for example, to fixate, secure, repair, and/or replace a fractured or dislocated bone fragment within the knee joint, the ankle joint, the shoulder joint, or the wrist joint. It would be well within the ordinary skill of the art, in this regard, to tailor or adjust the dimensions of particular components of the device described herein for use in conjunction with different bones or joints of the body or to change or adjust the steps of the method described herein for use in fixating or repairing different bones or joints of the body. For example, the ordinary skilled artisan would understand that the size and/or length of the anterior and posterior traversing elements, the number of guiding components, the size and/or length of the anterior and/or posterior hollow guide elements, and/or the location and/or orientation of the anterior and/or posterior hollow guide elements can be altered for use at different fracture and/or dislocation sites.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method for securing a coronoid process fragment to the remainder of a coronoid process of an ulna of a patient at a site of fracture using a device comprising:
    a frame component comprising at least one anterior traversing element that extends across the anterior side of the ulna of a patient, at least one posterior traversing element that extends across the posterior side of the ulna of the patient, and at least one connector element that operably connects the at least one anterior and the at least one posterior traversing elements in such a manner that the distance between the at least one anterior and the at least one posterior traversing elements is adjustable; and
    at least two guiding components, wherein each guiding component comprises
        (i) an anterior hollow guide element, which is situated on the at least one anterior traversing element in proximity to the site of fracture and is positionable such that it contacts and secures the coronoid process fragment to the remainder of the coronoid process of the ulna, and through which a surgical device can be passed, and
        (ii) a posterior hollow guide element, which is situated on the at least one posterior traversing element and is positionable such that it contacts a site on the posterior side of the ulna, and through which a surgical device can be passed, wherein the anterior and posterior hollow guide elements of each guiding component collectively define formable surgical repair channels through the coronoid process fragment and the remainder of the ulna for use in repair of the coronoid process fracture,
    wherein the method comprises:
    positioning the device such that the frame component extends across the ulna of the patient such that the anterior hollow guide elements of the at least two guiding components of the device are positioned in proximity to the site of fracture;
    adjusting the distance between the at least one anterior traversing element and the at least one posterior traversing element of the frame component, such that the anterior hollow guide elements of the at least two guiding components contact and substantially secure the coronoid process fragment to the remainder of the coronoid process of the ulna, and the posterior hollow guide elements of the at least two guiding components contact the posterior side of the ulna;
    forming at least two surgical repair channels through the coronoid process fragment and at least a portion of the ulna by passing a surgical device through the anterior hollow guide elements or the posterior hollow guide elements of the at least two guiding components; and
    fixing the coronoid process fragment to the remainder of the coronoid process through use of a surgical binding device in the surgical repair channels.

* * * * *